United States Patent [19]

Kitano et al.

[11] Patent Number: 4,816,188

[45] Date of Patent: Mar. 28, 1989

[54] PROCESS FOR THE PREPARATION OF SATURATED/UNSATURATED MIXED FATTY ACID ESTER SULFONATES

[75] Inventors: Kyozo Kitano, Narashino; Shizuo Sekiguchi, Funabashi, both of Japan

[73] Assignee: Lion Corporation, Tokyo, Japan

[21] Appl. No.: 185,355

[22] Filed: Apr. 18, 1988

Related U.S. Application Data

[63] Continuation of Ser. No. 54,039, May 26, 1987, abandoned, which is a continuation of Ser. No. 789,228, Oct. 18, 1985, abandoned.

[30] Foreign Application Priority Data

Oct. 20, 1984 [JP] Japan ............................... 59-221480

[51] Int. Cl.$^4$ ........................................... C07C 143/90
[52] U.S. Cl. ................................................... 260/400
[58] Field of Search ......................................... 260/400

[56] References Cited

U.S. PATENT DOCUMENTS 2,854,476 9/1958 Chenicek et al. .................. 260/505
4,545,939 10/1985 Sekiguchi et al. ................. 260/400

*Primary Examiner*—Anton H. Sutto
*Attorney, Agent, or Firm*—Armstrong, Nikaido, Marmelstein & Kubovcik

[57] ABSTRACT

A mixture of a saturated fatty acid ester sulfonate and an unsaturated fatty acid ester sulfonate, which is useful as an active ingredient of a detergent, is prepared at a stroke by sulfonating a mixture of a saturated fatty acid ester and an unsaturated fatty acid ester by using as a sulfonating agent a saturated fatty acid ester having $SO_3$ adsorbed therein in an amount larger than the equimolar amount, and then neutralizing the sulfonation product.

7 Claims, No Drawings

PROCESS FOR THE PREPARATION OF SATURATED/UNSATURATED MIXED FATTY ACID ESTER SULFONATES

This application is a continuation of Ser. No. 54,039, filed May 26, 1987, which is a continuation of Ser. No. 789,228, filed Oct. 18, 1985, both now abandoned.

BACKGROUND OF THE INVENTION

1. Field of the Invention

The present invention relates to a process for preparing at a stroke a saturated/unsaturated mixed fatty acid ester sulfonate, that is, a mixture of a saturated fatty acid ester sulfonate and an unsaturated fatty acid ester sulfonate.

A saturated fatty acid ester sulfonate and an unsaturated fatty acid ester sulfonate are valuable as surface active agents even when used alone, but a mixture of both sulfonates is almost ideal as an active ingredient of a detergent because the mixture has an excellent foaming property, cleansing power and permeating property, and a good rinsing property.

2. Description of the Related Art

As a most common means for preparing a saturated-/unsaturated mixed fatty acid sulfonate having the above-mentioned characteristics, there is considered a process comprising sulfonating a mixture of a saturated fatty acid ester and an unsaturated fatty acid ester (hereinafter referred to as a saturated/unsaturated mixed fatty ester). However, the saturated fatty acid ester and the unsaturated fatty acid ester are greatly different in their reactivity to sulfonation, namely, the reactivity of the unsaturated fatty acid ester is higher than that of the saturated fatty acid ester. Accordingly, when a mixture of both esters is sulfonated according to a customary procedure, the unsaturated fatty acid ester is preferentially sulfonated, and if the reaction is continued until the saturated fatty acid ester is sulfonated, the unsaturatd fatty acid ester is polysulfonated and the color of the reaction product is degraded. If sulfonation is carried out under mild conditions such that degradation of the color of the product can be avoided, a satisfactory conversion cannot be attained with respect to the saturated fatty acid ester.

Accordingly, when a saturated/unsaturated mixed fatty acid ester sulfonate is desired, a process is inevitably adopted in which the respective fatty acid esters are independently sulfonated and the respective sulfonation products are neutralized, and the thus-obtained sulfonates are then mixed. When a saturated fatty acid ester alone is used, sulfonation can be accomplished relatively easily according to a process as disclosed in Japanese Examined Patent Publication Nos. 39-20482, 39-28635 or 41-965. However, in the case of an unsaturated fatty acid ester, because of the high reactivity, control of the reaction conditions is difficult, and if a known process as disclosed in the above patent publications is adopted, it is impossible to obtain a light-color sulfonation product in a high yield.

Note, the specification of British Patent No. 1,278,421 discloses a process for the film sulfonation of an unsaturated fatty acid. However, if this process is applied to the sulfonation of an unsaturated fatty acid ester, it is impossible to obtain a light-color sulfonation product in a high yield.

SUMMARY OF THE INVENTION

Under the above-mentioned background, it is a primary object of the present invention to provide a process for preparing at a stroke a saturated/unsaturated fatty acid ester sulfonate which is suitable as an active ingredient of a detergent.

In accordance with the present invention, there is provided a process for the preparation of saturated/unsaturated mixed fatty acid ester sulfonates, wherein a saturated/unsaturated mixed fatty acid ester is sulfonated by using as a sulfonating agent a saturated fatty acid ester having $SO_3$ absorbed therein in an amount larger than the equimolar amount and then the sulfonation product is neutralized.

DESCRIPTION OF THE PREFERRED EMBODIMENTS

The carbon number of the saturated fatty acid ester used in the present invention need not be the same as the carbon number of the unsaturated fatty acid ester used in the present invention. At least one member from linear and branched fatty acid alkyl esters having 6 to 24 carbon atoms in the fatty acid residue and 1 to 10 carbon atoms in the alkyl group ester-linked thereto may be used as the saturated fatty acid ester and the unsaturated fatty acid ester. The unsaturated fatty acid esters preferably have 1 to 5 double bonds. The saturated fatty acid ester in which $SO_3$ is absorbed in an amount larger than the equimolar amount may or may not be the same as the saturated fatty acid ester in the saturated/unsaturated mixed fatty acid ester to be reacted with the thus-prepared sulfonating agent.

The sulfonating agent of the present invention can be prepared by absorbing $SO_3$ in an amount larger than the equimolar amount, that is, in an amount of 1.1 to 5.0 moles, preferably 1.5 to 3.0 moles, into the saturated fatty acid ester maintained at a temperature higher than the solidification point but no higher than 150° C. If the amount of $SO_3$ absorbed in the saturated fatty acid ester is smaller than 1.1 moles per mole of the ester, the unsaturated fatty acid cannot be sufficiently sulfonated. If the amount of abosorbed $SO_3$ is larger than 5 moles per mole of the ester, formation of the polysulfonation product is increased and the color of the reaction product is degraded. It is presumed that, in the sulfonating agent of the present invention formed by absorbing $SO_3$ in the saturated fatty acid ester in an amount larger than the equimolar amount, the excess of $SO_3$ is dissolved in an adduct of 1 mole of $SO_3$ to the saturated fatty acid ester while forming a complex with the adduct.

In the saturated/unsaturated fatty acid ester to be reacted with the above-mentioned sulfonation product, the saturated fatty acid ester/unsaturated fatty acid ester weight ratio can be optionally selected within the range of from 95/5 to 5/95. However, the amount of the saturated/unsaturated mixed fatty acid ester to be used for the reaction can be adjusted so that the value A defined by the following formula is 0.8 to 5.0, preferably 1.0 to 3.0.

$$A = (a-b)/c$$

where
 a: moles of $SO_3$ used for the preparation of the sulfonating agent,
 b: moles of the saturated fatty acid ester used for the preparation of the sulfonating agent, and, c: moles of the unsaturated fatty acid ester in the mixed fatty acid ester.

It is preferred that the reaction temperature be maintained at a level higher than the solidification point of the mixed fatty acid ester but not higher than 150° C. The reaction time is selected so that the unsaturated fatty acid ester in the mixed fatty acid ester is sufficiently sulfonated. This reaction time depends on the amount of $SO_3$ absorbed in the sulfonating agent, the mixing ratio in the mixed fatty acid ester, the amount of the mixed fatty acid ester used, and the reaction temperature. Generally, the reaction time is 1 to 120 minutes.

After termination of the sulfonation reaction, the sulfonation reaction mixture is treated by appropriate means such as settling separation, centrifugal separation, extraction with solvent, and film topping to separate the unreacted substance composed mainly of the saturated fatty acid ester from the sulfonation product. Then, the sulfonation product is neutralized by customary procedures using a solution of an oxide or hydroxide of an alkali metal such as lithium, sodium or potassium or an alkaline earth metal such as magnesium or barium, whereby the intended saturated/unsaturated mixed fatty acid ester sulfonate can be obtained. In the above-mentioned embodiment, after the unreacted substance has been separated from the sulfonation reaction mixture, the sulfonation product is neutralized. A modification may be adopted in which the sulfonation reaction mixture is neutralized before the separation of the unreacted substance and the unsulfonated substance is then separated.

As is apparent from the foregoing description, according to the present invention, by using as the sulfonating agent a saturated fatty acid ester having $SO_3$ absorbed therein in an amount larger than the equimolar amount and reacting a saturated/unsaturated fatty acid ester with this sulfonating agent, a sulfonation product of a saturated fatty acid ester and a sulfonation product of an unsaturated fatty acid ester are simultaneously obtained, and by neutralizing the resulting sulfonation product according to customary procedures, a light-color saturated/unsaturated mixed fatty acid ester suitable as an active ingredient of a detergent can be obtained in a high yield. In carrying out the process of the present invention, the unsulfonated substance, that is, the saturated fatty acid ester, is recovered from the sulfonation reaction mixture. If $SO_3$ is absorbed in the recovered ester in an amount larger than the equimolar amount, the product can be used as the sulfonating agent of the present invention. Accordingly, in the present invention, it is preferred that the saturated fatty acid ester used for the preparation of the sulfonating agent be the same as the saturated fatty acid ester in the mixed fatty acid ester to be sulfonated.

The present invention will now be described in detail with reference to the following examples that by no means limit the scope of the invention.

EXAMPLE 1

In a film type reaction vessel made of a laboratory glass, $SO_3$ was absorbed in methyl stearate at 80° C. in an amount of 2.5 moles per mole of methyl stearate, and the mixture was aged for 20 minutes at the same temperature to obtain the sulfonating agent of the present invention.

An Erlenmeyer flask having a capacity of 500 ml was charged with 100 g of the sulfonating agent, and 91.9 g of a methyl stearate/methyl oleate mixed ester (mixing weight ratio=1/1) was added (the value A was larger than 2). Reaction was carried out at 40° C. with stirring for 60 minutes. Then, the reaction mixture was neutralized by a 10% aqueous solution of NaOH, and unreacted methyl stearate was removed by topping to obtain a mixed ester sulfonate.

The color and conversion of the thus-obtained mixed ester sulfonate and the iodine value of unreacted methyl stearate were determined to obtained the following results.

Color (1% aqueous solution)—950
Conversion (ether extraction method)—94%
Iodine value of unreacted substance—0.6

As is seen from the iodine value of the unreacted substance, the recovered methyl stearate could be used again for the preparation of the sulfonating agent.

EXAMPLES 2 THROUGH 10

The procedures of Example 1 were repeated in the same manner except that the material to be sulfonated and the sulfonation conditions were changed as shown in Table 1. The obtained results are shown in Table 1.

The symbols used in Tables 1 and 2 have the following meanings.

SM=methyl stearate
OM=methyl oleate
PM=methyl palmitate
CM=methyl caprylate
$A=(a-b)/c$ where
a=moles of $SO_3$ used for the preparation of the sulfonating agent,
b=moles of the saturated fatty acid ester used for the preparation of the sulfonating agent, and
c=moles of the unsaturated fatty acid ester in the mixed fatty acid ester.

TABLE 1

| | Example No. | | | | | | | | |
|---|---|---|---|---|---|---|---|---|---|
| | 2 | 3 | 4 | 5 | 6 | 7 | 8 | 9 | 10 |
| Sulfonating agent | | | | | | | | | |
| Ester | SM | PM | PM | Methyl ester of highly hardened fish oil fatty acid | Methyl ester of highly hardened palm oil fatty acid | Methyl ester of highly hardened beef tallow fatty acid | CM | SM | SM |
| $SO_3$/ester molar ratio | 2.0 | 2.5 | 1.5 | 3.0 | 2.5 | 2.5 | 4.5 | 2.0 | 2.0 |
| $SO_3$-absorbing temperature (°C.) | 80 | 80 | 70 | 80 | 80 | 80 | 60 | 45 | 110 |
| Material to be sulfonated | | | | | | | | | |
| Mixed ester, weight ratio | OM/SM = 3/7 | OM/SM = 1/1 | OM/SM = 2/8 | Methyl ester of fish oil | Methyl ester of palm oil | Methyl ester of beef | Methyl ester of palm oil | SM/OM = 1/1 | SM/OM = 1/1 |

TABLE 1-continued

| | Example No. | | | | | | | | |
|---|---|---|---|---|---|---|---|---|---|
| | 2 | 3 | 4 | 5 | 6 | 7 | 8 | 9 | 10 |
| | | | | fatty acid | fatty acid | tallow fatty acid | fatty acid | | |
| Value A | 1.5 | 2.0 | 1.5 | 3.0 | 2.0 | 2.0 | 4.5 | 2.0 | 2.0 |
| Reaction temperature (°C.) | 50 | 40 | 40 | 40 | 40 | 40 | 40 | 40 | 40 |
| Sulfonate | | | | | | | | | |
| Color | 750 | 870 | 770 | 1300 | 960 | 1050 | 1800 | 850 | 2100 |
| Conversion (%) | 96 | 95 | 95 | 95 | 96 | 95 | 95 | 94 | 96 |
| Iodine value of unreacted oil | 0.7 | 0.5 | 0.5 | 0.5 | 0.6 | 0.7 | 0.5 | 0.7 | 0.5 |
| Evaluation | Good | Good | Good | Good | Good | Good | Good | Good | Fairly good |

COMPARATIVE EXAMPLE 1

In a film type reaction vessel made of a laboratory glass, a methyl stearate/methyl oleate mixed ester (mixing weight ratio=1/1) was sulfonated at a reaction temperature of 80° C. with $SO_3$ in an amount of 5.0 moles per mole of the mixed ester, and the reaction mixture was aged at 80° C. for 20 minutes. Then, the sulfonation product was neutralized with a 10% aqueous solution of NaOH.

The color and conversion of the obtained sulfonate were determined in the same manner as in Example 1 to obtain the following results.

Color (1% aqueous solution)—6000
Conversion (ether extraction method)—65%

COMPARATIVE EXAMPLES 2 THROUGH 8

The procedures of Example 1 were repeated in the same manner except that the material to be sulfonated and sulfonation conditions were changed as shown in Table 2. The obtained results are shown in Table 2.

TABLE 2

| | | Comparative Example No. | | | | | | |
|---|---|---|---|---|---|---|---|---|
| | | 2 | 3 | 4 | 5 | 6 | 7 | 8 |
| Sulfonating agent | Ester | PM | PM | SM | SM | SM | SM | PM |
| | $SO_3$/ester molar ratio | 1.2 | 6.5 | 2.0 | 2.5 | 2.5 | 2.5 | 2.5 |
| | $SO_3$-absorbing temperature (°C.) | 80 | 80 | 160 | 80 | 80 | 80 | 80 |
| Material to be sulfonated | Mixed ester, weight ratio | OM/PM = 1/1 | OM/PM = 1/1 | SM/OM = 1/1 | SM/OM = 1/1 | SM/OM = 1/1 | SM/OM = 8/2 | OM/PM = 1/1 |
| | Value A | 0.7 | 1.5 | 2.0 | 2.0 | 2.0 | 2.0 | 5.5 |
| | Reaction temperature (°C.) | 40 | 40 | 40 | 10 | 160 | 160 | 40 |
| Sulfonate | Color | 650 | 7500 | 4800 | — | 8500 | 7600 | 9000 |
| | Conversion (%) | 95 | 95 | 96 | — | 96 | 94 | 96 |
| Iodine value of unreacted oil | | 9.5 | 0.4 | 0.5 | | 0.4 | 0.3 | 0.3 |
| Evaluation | | Poor | Poor | Poor | — | Poor | Poor | Poor |

As is apparent from the results shown in Table 2, even if a process similar to the process of the present invention is adopted, if the value A is too small (Comparative Example 2) or too large (Comparative Example 8), the amount of $SO_3$ used for formation of the sulfonating agent is too large (Comparative Example 3), the temperature adopted for absorption of $SO_3$ for the preparation of the sulfonating agent is too high (Comparative Example 4) or the sulfonation reaction temperature is too high (Comparative Examples 6 and 7), the intended product cannot be obtained.

In Comparative Example 5, since the solidification point of the mixed ester was 25° C., it was impossible to advance the sulfonation reaction at a reaction temperature of 10° C.

We claim:

1. A process for the preparation of a mixture of a saturated fatty acid ester sulfonate and an unsaturated fatty acid ester sulfonate, which comprises sulfonating a mixture of a saturated fatty acid ester and an unsaturated fatty acid ester, in a weight ratio in the range of 95/5 to 5/95, by using as a sulfonating agent a saturated fatty acid ester having $SO_3$ absorbed therein in an amount larger than the equimolar amount, and then neutralizing the sulfonation product.

2. A process according to claim 1 wherein said mixture of a saturated fatty acid ester and an unsaturated fatty acid ester is a mixture of a saturated fatty acid alkyl ester having 6 to 24 carbon atoms in the fatty acid residue and 1 to 10 carbon atoms in the alkyl group ester-linked thereto and an unsaturated fatty acid alkyl ester having 6 to 24 carbon atoms in the fatty acid residue and 1 to 10 carbon atoms in the alkyl group ester-linked thereto and having 1 to 5 double bonds.

3. A process according to claim 1 wherein the saturated fatty acid ester having $SO_3$ absorbed therein is prepared by absorbing 1.1 to 5.0 moles, per mole of the saturated fatty acid ester, of $SO_3$ into the saturated fatty acid ester.

4. A process according to claim 3 wherein the amount of $SO_3$ absorbed into the saturated fatty acid ester is in the range of 1.5 to 3.0 moles per mole of the saturated fatty acid ester.

5. A process according to claim 1 wherein the saturated fatty acid ester having $SO_3$ absorbed therein is used in an amount such that a value A defined by the following equation is in the range of 0.8 to 5.0:

$$A = (a-b)/c$$

where a: moles of SO₃ used for the preparation of the sulfonating agent,
b: moles of the saturated fatty acid ester used for the preparation of the sulfonating agent, and
c: moles of the unsaturated fatty acid ester in the mixed fatty acid ester.

6. A process according to claim 5 wherein the value A is in the range of 1.0 to 3.0.

7. A process according to claim 1 wherein the sulfonation is carried out at a temperature higher than the solidification point of the fatty acid ester mixture but not higher than 150° C.

* * * * *